United States Patent
Kikuchi

[11] Patent Number: 6,067,402
[45] Date of Patent: May 23, 2000

[54] HEATING UNIT FOR VAPORIZING SAMPLE BY HEATING

[75] Inventor: Fumihide Kikuchi, Tokyo, Japan

[73] Assignee: Kett Electric Laboratory, Tokyo, Japan

[21] Appl. No.: 09/141,524

[22] Filed: Aug. 27, 1998

[30] Foreign Application Priority Data

Aug. 29, 1997 [JP] Japan ................................ 9-234190

[51] Int. Cl.[7] .......................... A01G 13/06; G01N 30/02; G01N 1/00
[52] U.S. Cl. ...................... 392/386; 73/23.35; 73/863.11
[58] Field of Search .................. 392/386, 394, 392/405; 73/19.1, 19.01, 23.35, 23.41, 863.11, 863.12, 863.21, 863.85, 864.83, 864.86, 864.87

[56] References Cited

U.S. PATENT DOCUMENTS

| | | | |
|---|---|---|---|
| 4,096,734 | 6/1978 | Khayat | 73/23.1 |
| 4,276,243 | 6/1981 | Partus | 392/396 |
| 4,640,221 | 2/1987 | Barbee et al. | 118/715 |
| 4,838,705 | 6/1989 | Byers, Jr. et al. | |
| 5,191,211 | 3/1993 | Gorman, Jr. | 73/23.35 |
| 5,396,812 | 3/1995 | Peterson | 73/863.81 |
| 5,672,810 | 9/1997 | Shibamoto | 73/23.25 |

*Primary Examiner*—Sang Paik
*Attorney, Agent, or Firm*—Wenderoth, Lind & Ponack, L.L.P.

[57] ABSTRACT

A heating unit vaporizes a sample placed in a container having an opening that is hermetically sealed with a rubber gasket and discharges the vaporized constituents to the outside of the container together with a carrier gas. A sample 16, such as an easy-to-vaporize liquid, is placed in a container 1 whose opening 1a is hermetically sealed with a rubber gasket 2a. The container 1 is loaded into a heating tube 8 to extract the vaporizable constituents. The heating tube 8 is equipped with carrier gas introduction tubes 12 having needles 4 with through-holes, a vaporized constituent and carrier gas discharge tube 13 having a needle 5 with a through-hole, and a heater 11. These needles 4 and 5 are arranged to pierce the rubber gasket 2a of the container 1 placed in the heating tube 8.

2 Claims, 5 Drawing Sheets

F I G . 1
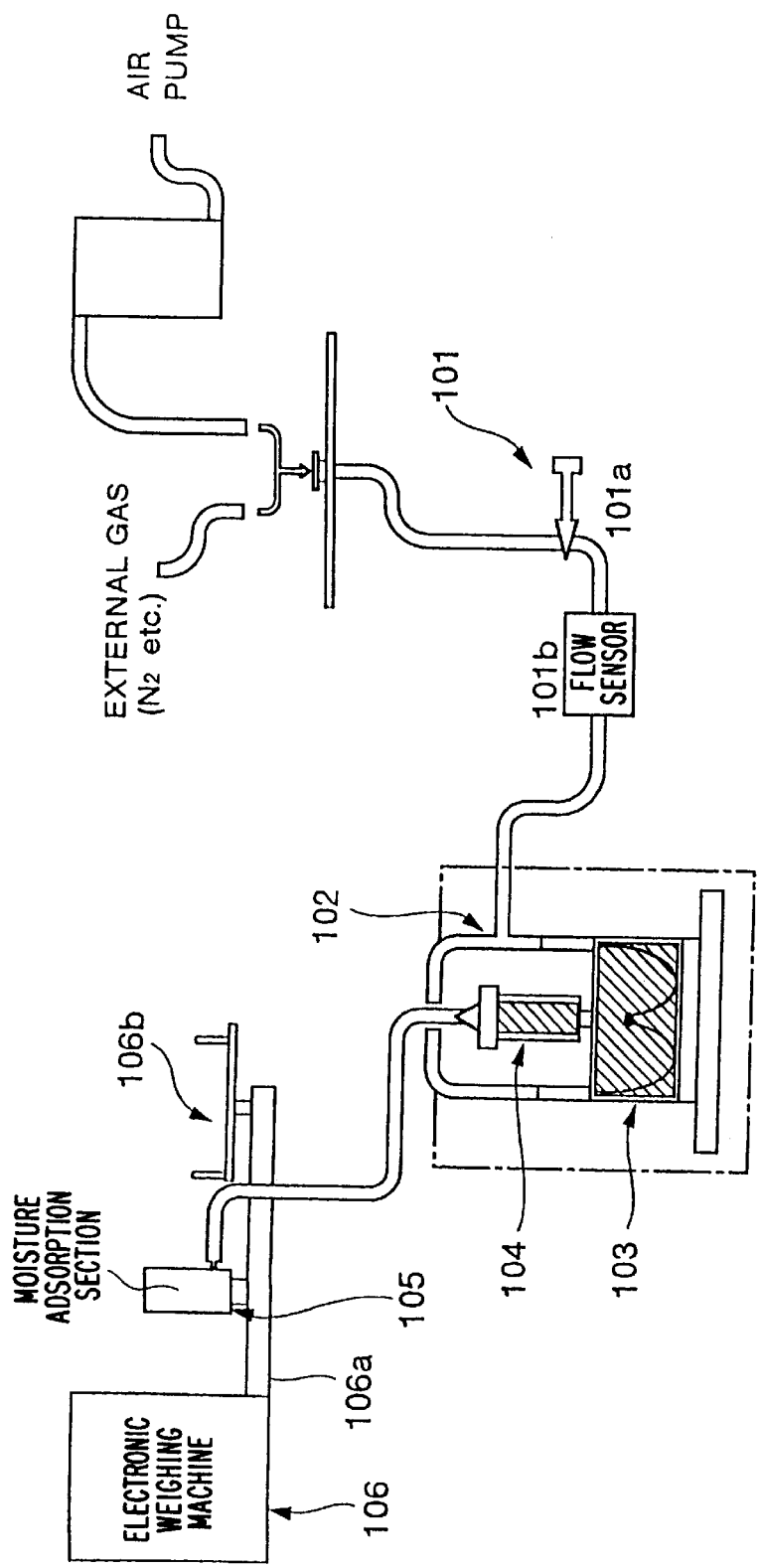

F I G. 3
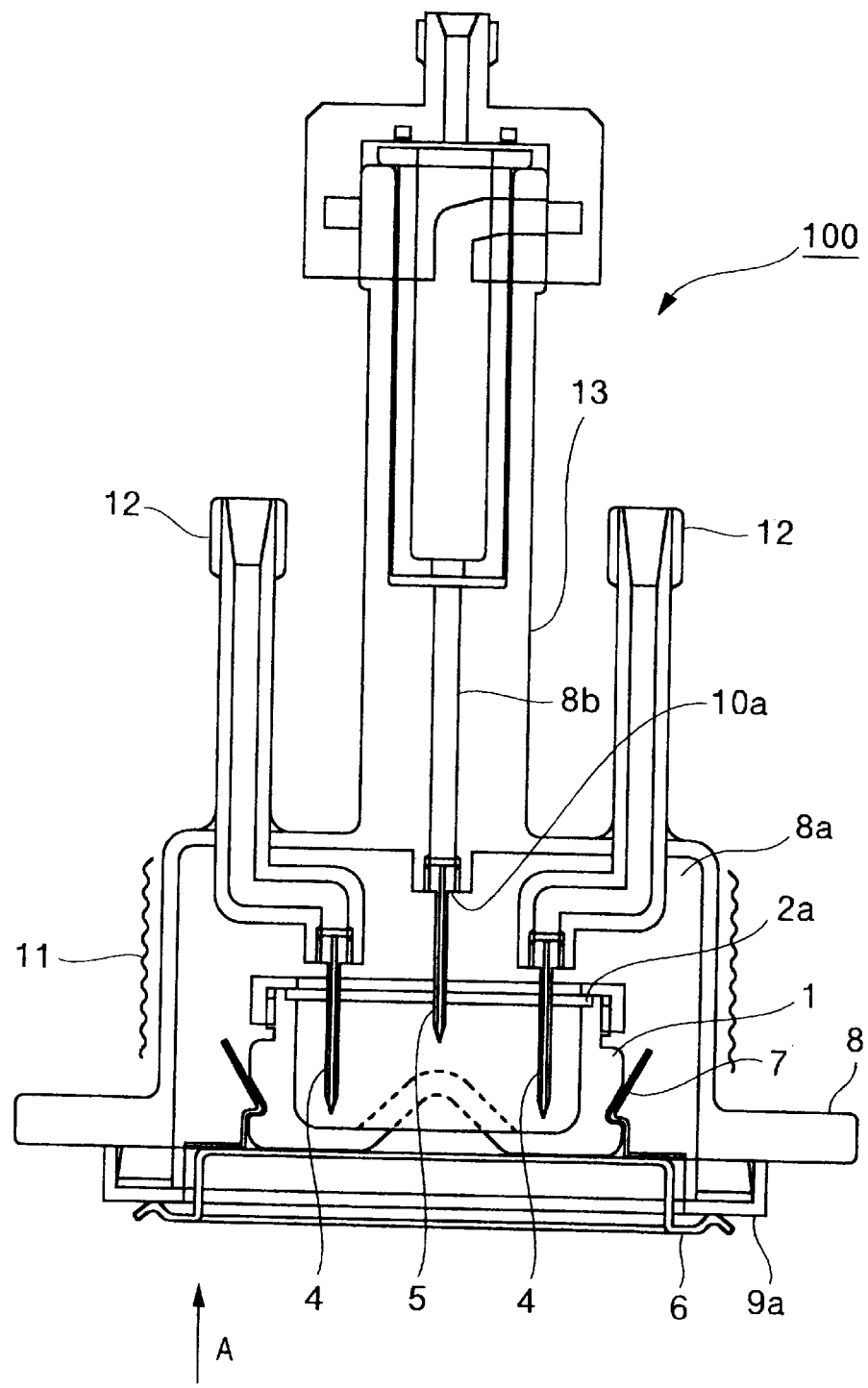

HEATING UNIT FOR VAPORIZING SAMPLE BY HEATING

BACKGROUND OF THE INVENTION

1. Field of the Invention

The present invention relate to a heating unit for vaporizing a sample by heating; in detail, to a heating unit that, by heating, vaporizes the sample placed in a container whose opening is hermetically sealed with a rubber gasket, and discharges vaporized constituents to the outside of the container together with a carrier gas.

The present invention is applicable as a heating unit for use with a moisture meter that vaporizes the moisture in the test sample by heating, carries it with the carrier gas, and collects and detects only the vaporized moisture to determine the moisture content of the test sample.

2. Prior Art

This type of heating unit in the conventional technology provides a sample chamber containing the test sample, and is equipped with a heating chamber having a means to heat the sample chamber, an introduction tube to introduce the carrier gas into the test sample in the chamber, a discharge tube to discharge the vaporized constituents and the carrier gas to the outside of the sample chamber, and a sealing means to hermetically seal the chamber in which the sample is loaded.

SUMMARY OF THE INVENTION

With a heating unit of the conventional technology as stated above, when a sample, such as an easy-to-vaporize liquid, is heated, it is vaporized before being heated, which presents a problem in that, if the heating unit is used with a moisture meter, accurate measurement cannot be made.

A sample, such as an easy-to-vaporize liquid, can be placed in a hermetically sealed container. However, another problem is applying the carrier gas to the sample placed in the hermetically sealed container, and extracting the vaporized constituents, successfully.

The present invention solves such problems with ease, and offers a heating unit that can easily and exactly extract the constituents vaporized from a sample such as an easy-to-vaporize liquid.

A sample 16, such as an easy-to-vaporize sample, is placed in a container 11 whose opening 1a is hermetically sealed with a rubber gasket 2a, and the container 11 is loaded in a heating tube 8 to extract vaporizable constituents. The heating tube 8 is equipped with carrier gas introduction tubes 12 having needles 4 with through-holes, a vaporized constituent and carrier gas discharge tube 13 having a needle 5 with a through-hole, and a heating means 11. The needles 4 and 5 are arranged to pierce the rubber gasket 2a for the container 1 placed in the heating tube 8.

BRIEF DESCRIPTION OF THE DRAWINGS

FIG. 1 is a block diagram illustrating the path of a fluid system in and the function of a moisture meter for which a heating unit of the present invention can be utilized.

FIG. 3 is a sectional view showing the outline of a heating unit as a second aspect of and embodiment of the present invention.

Figure 2:
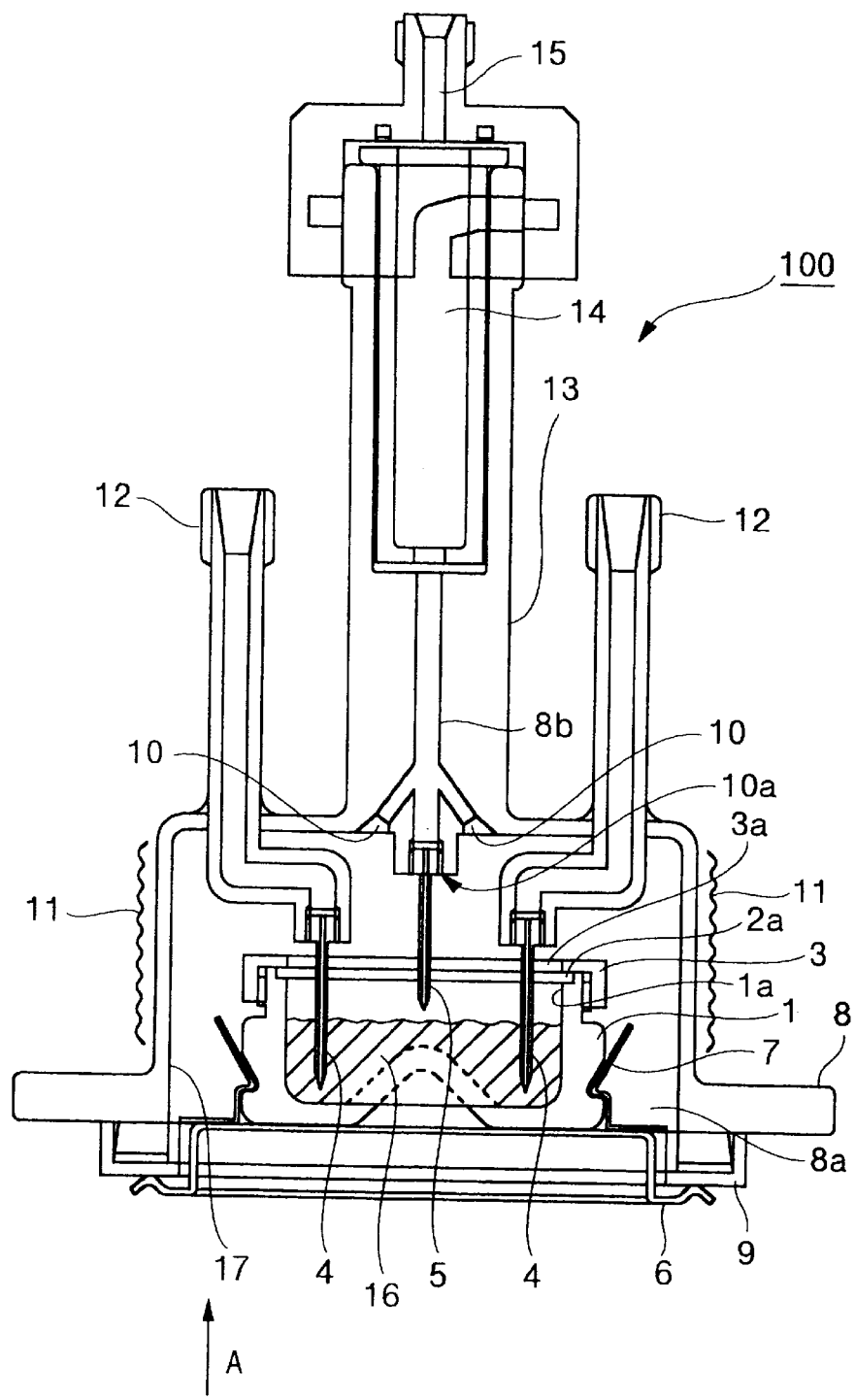
FIG. 2 is a sectional view showing an outline of a heating unit as one aspect of embodiment of the present invention.

DESCRIPTION OF REFERENCE NOS.

1 Container
1a Opening
2a Rubber gasket
2b Rubber gasket having some permeability
3 Cover
3a Opening
4 Needle having a through-hole
5 Needle having a through-hole
6 Sample tray
7 Catch
8 Heating tube
8a Chamber
8b Discharge path
9 Sealing
9a Interposing member
10 Port
10a Port
11 Heater
12 Introduction tube
13 Discharge tube
14 Filter unit
15 Passage
16 Liquid sample
17 Opening
100 Heating unit
101 Control section
101a Needle valve
101b Flow sensor
102 Heating unit
103 Heating tube
104 Filter unit
105 Moisture adsorption section
106 Electronic weighing machine
106a Weighing arm
106b Test sample weighing section

DETAILED DESCRIPTION OF THE INVENTION

The reference Nos. used in the later section entitled "Aspects of Embodiment of Present Invention" are also used here. The present invention is characterized in that it provides a heating unit which, by heating, vaporizes a sample placed in a container 1 whose opening 1a is hermetically sealed with a rubber gasket 2a, and discharges the vaporized constituents to the outside of the container 1 together with a carrier gas. A chamber 8a accommodates the container 1, and includes a heating tube 8 with a heating means 11 to heat the inside of the chamber 8a. Introduction tubes 12 introduce the carrier gas from the outside of the chamber 8a into the container 1 placed in the chamber 8a. A discharge tube 13 discharges the vaporized constituents and the carrier gas from the container 1 placed in the chamber 8a to the outside of the chamber 8a. The introduction tubes 12 are each equipped with a needle 4 having a through-hole at the respective ends to pierce the rubber gasket 2a for the container 1 for introduction of the carrier gas into the container 1. The discharge tube 13 is equipped with a needle 5 having a through-hole at the end to pierce the rubber gasket 2a for the container 1 for discharge of the vaporized constituents and the carrier gas in the container 1.

In addition, the present invention may have the rubber gasket be a rubber gasket 2b having permeability, with a seal 9 hermetically sealing the chamber 8a loaded with the container 1.

Further, the present invention is characterized in that it provides a heating unit which, by heating, vaporizes the constituents of an easy-to-vaporize liquid sample placed in the container 1 whose opening 1a is hermetically sealed with the rubber gasket 2b having permeability, and discharges the vaporized constituents to the outside of the container 1 together with the carrier gas. The chamber 8a accommodates the container 1 and includes the heating tube 8 with heating means 11 to heat the inside of the chamber 8a. Introduction tubes 12 introduces the carrier gas from the outside of the chamber 8a into the container 1 placed in the chamber 8a.

The discharge tube 13 discharges the vaporized constituents and the carrier gas from the chamber 8a to the outside of the chamber 8a. The seal 9 hermetically seals the chamber 8a loaded with the container 1. The introduction tubes 12 are equipped with the needles 4 having through-holes at the respective ends to pierce the rubber gasket 2b for the container 1 for introduction of the carrier gas into the container 1.

Aspects of the Embodiments of the Present Invention

By referring to FIG. 1, the outline of a moisture meter for which the present invention can be utilized will be described. FIG. 1 is a block diagram illustrating the path of a fluid system in the moisture meter and its function. A control section 101 has a needle valve 101a for adjusting the flow rate of the carrier gas, and a flow sensor 101b for determining the flow rate of the carrier gas delivered to the heating unit 102.

The heating unit as shown in FIG. 1 is of the prior art as described above, and the carrier gas is introduced into a heating tube 103 in which the sample is loaded. The sample in the heating tube 103 is heated and dried by heating means (not shown). The constituents vaporized by heating from the sample in the heating tube 103 are introduced into a filter unit 104 together with the carrier gas, where the carrier gas carrying the vaporized moisture and gases is purged of gases other than the vaporized moisture. The carrier gas carrying the vaporized, moisture flowing out of the filter unit 104 is fed into the moisture adsorption section 105, where only, the vaporized moisture is adsorbed. The weighing arm 106a of the electronic weighing machine 106 is equipped with a moisture adsorption section 105 and a test sample weighing section 106b to not only determine the moisture content of the test sample, but also to measure the mass of the test sample itself.

The present invention modifies the heating unit including the heating tube 103 to allow samples, such as easy-to-vaporize liquid samples, to be measured. FIG. 2 is a sectional view showing the outline of a heating unit as one aspect of an embodiment of the present invention.

FIG. 2 shows the container 1 having the sample 16 being heated, placed in the chamber 8a in the heating tube 8 in the heating unit 100. The heating tube 8 is upright and cylindrical, having an opening 17 at the bottom. The sample tray 6 on which the container 1 is loaded is partially fitted into the opening 17, and a seal 9 is interposed between the sample tray 6 and the periphery of the opening 17 of the heating tube 8 so that, when the sample dish 6 is fitted into the opening 17, the chamber 8a of the heating tube 8 is hermetically sealed. The sample tray 6 is equipped with a catch 7, which firmly fixes the container 1 on the sample tray 6.

The container 1 has an opening 1a at the top, and a rubber gasket 2a is placed at the opening 1a to seal the container 1. The rubber gasket 2a is fixed with a cover 3 having an opening 3a.

On the periphery of the heating tube 8, a heater 11 is provided to heat the inside of the chamber 8a. The heating tube 8 is equipped with introduction tubes 12 (two for the unit as shown in FIG. 2) to introduce the carrier gas. The ends of the introduction tubes 12 that are in the chamber 8a are each equipped with a needle 4 having a throughhole. The needle 4 may either be designed to be screwed into the introduction tube 12 or to be fitted there-into with an O-ring. The needles 4 pierce the rubber gasket 2a covering the opening 1a of the container 1 to introduce the carrier gas fed through the introduction tubes 12 into the lower area of the sample 16 in the container 1 for promoting vaporization of the sample 16. When the sample is liquid, it is bubbled for promotion of vaporization.

In the central area at the top of the heating tube is a discharge tube 13 provided with a discharge path 8b to discharge the vaporized constituents and the carrier gas to the outside of the chamber 8a. The discharge path 8b has, at its lower end, ports 10 connecting to the chamber 8a, and a port 10a provided with a needle 5 having a through-hole. The needle 5 may either be designed to be screwed into the discharge tube 13 or to be fitted there-into with an O-ring. The needle 5 pierces the rubber gasket 2a covering the opening 1a of the container 1 to discharge the vaporized constituents and the carrier gas in the container 1 to the outside of the chamber 8a through the discharge path 8b. The discharge tube 13 is connected to the filter unit 14, where the unnecessary gases are removed and the carrier gas carrying the vaporized moisture is passed through the path 15 to the moisture adsorption section as stated above with reference to FIG. 1.

Here is a description of the operation of this heating unit 100. For a liquid sample that is easy-to-vaporize, a tool such as a syringe is used to inject it into the container 1, which is hermetically sealed with the rubber gasket 2a and the cover 3, and the container I is fixed on the sample tray 6 by means of the catch 7. Then, after the mass of this sample is measured with the electronic weighing machine as discussed above, the sample tray 6 on which the container 1 is loaded is transferred to below the opening 17 of the heating tube 8. Then, a lift (not shown) raises the sample tray 6 in the direction of arrow A, and the seal 9 is interposed between the sample tray 6 and the periphery of the opening 17 of the heating tube 8 to hermetically seal the chamber 8a. When the sample 6 is raised in the direction of arrow A, the needles 4 and the needle 5 pierce the rubber gasket 2a of the container so that the tips of the needles 4 are positioned under the level of the liquid sample 16, while the tip of the needle 5 is above the level of the liquid sample 16.

For a sample 16 other than liquid, the sample is placed in the container 1, which is then hermetically sealed with the rubber gasket 2 and the cover 3, and is fixed on the sample tray 6 with the catch 7. Then, after the mass of this sample is measured with the electronic weighing machine, the sample tray 6 on which the container 1 is loaded is transferred to below the opening 17 of the heating tube 8. Then, the lift (not shown) raises the sample tray 6 in the direction of arrow A, and the seal 9 is interposed between the sample tray 6 and the periphery of the opening 17 of the heating tube 8 to hermetically seal the chamber 8a. When the sample 6 is raised in the direction of arrow A, the needles 4 and the needle 5 pierce the rubber gasket 2a of the container so that the tips of the needles 4 are positioned under the level of the sample 16, while the tip of the needle 5 is above the level of the sample 16.

This state is shown in FIG. 2. The carrier gas is introduced through the introduction tube 12 with the heater 11 being energized to heat the sample 16 in the container 1. Thus, the vaporized constituents and the carrier gas filling the container 1 are discharged from the discharge tube 13 to the outside of the heating unit 8 through the needle 5. The vaporized constituents and the carrier gas filling the chamber 8a are discharged from the discharge tube 13 to the outside through the port 10.

The unit as shown in FIG. 2 has been described based on the assumption that the rubber gasket 2a covering the opening 1a of the container 1 has no permeability. Practically, no part of the vaporized constituents and the carrier gas leaks into the chamber 8a through between the needles 4 and 5 and the rubber gasket 2a, and thus, if such a rubber gasket 2a having no permeability is used, the need for providing a port 10 as shown in FIG. 2 is eliminated, and the chamber 8a need not always be hermetically sealed with a sealing 9. FIG. 3 shows a heating unit 100 when a rubber gasket 2a having no permeability is provided for the container 1. With this unit, no ports 10 are provided, and the seal 9 in FIG. 2 is replaced with an interposing member 9a to firmly fix the sample tray 6 to the heating tube 8. The interposing member 9a need not serve to hermetically seal the chamber 8a. In FIG. 3, the same reference Nos. as those used in FIG. 2 denote the same or equivalent portions as those in FIG. 2, thus, description of them is omitted.

Figure 4:
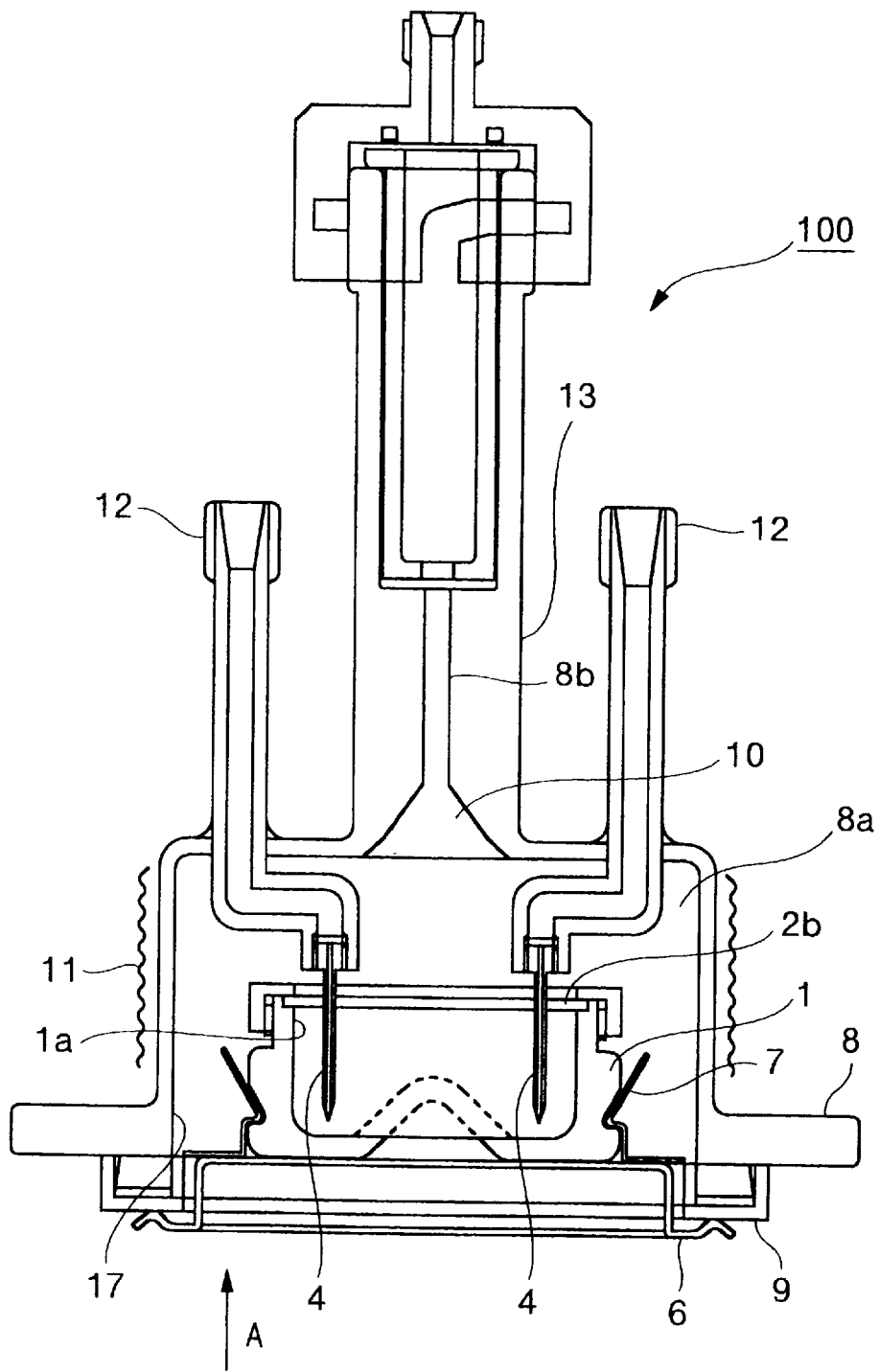
FIG. 4 is a sectional view showing the outline of a heating unit as a third aspect of an embodiment of the present invention.

However, if a configuration such as shown in FIG. 3 is adopted, a problem of the vaporized constituents and the carrier gas filling the area above the tip of the needle 5 are not easily discharged from the container 1 is presented, and it takes a long time for discharge. To solve this problem, the rubber gasket of the container 1 may be a rubber gasket 2a having some degree of permeability. FIG. 4 is a sectional view of a heating unit 100 that adopts such a configuration.

In FIG. 4, the same reference Nos. as those given in FIGS. 2 and 3 denote the same or equivalent portions. With the heating unit as shown in FIG. 4, the discharge tube 13 is not provided with a needle having a through-hole, and the port 10 is directly opened to the chamber 8a of the heating tube 8. The opening 1a of the container 1 is covered with a rubber gasket 2b having some degree of permeability, and the constituents vaporized in the container 1 and the carrier gas are passed into the chamber 8a through the rubber gasket 2b having some degree of permeability and discharged to the outside of the chamber 8a through the port 10. Because of this configuration, the seal 9 must, of course, be designed so that it can hermetically seal the chamber 8a being interposed between the sample tray 6 and the periphery of the opening 17.

Figure 5:
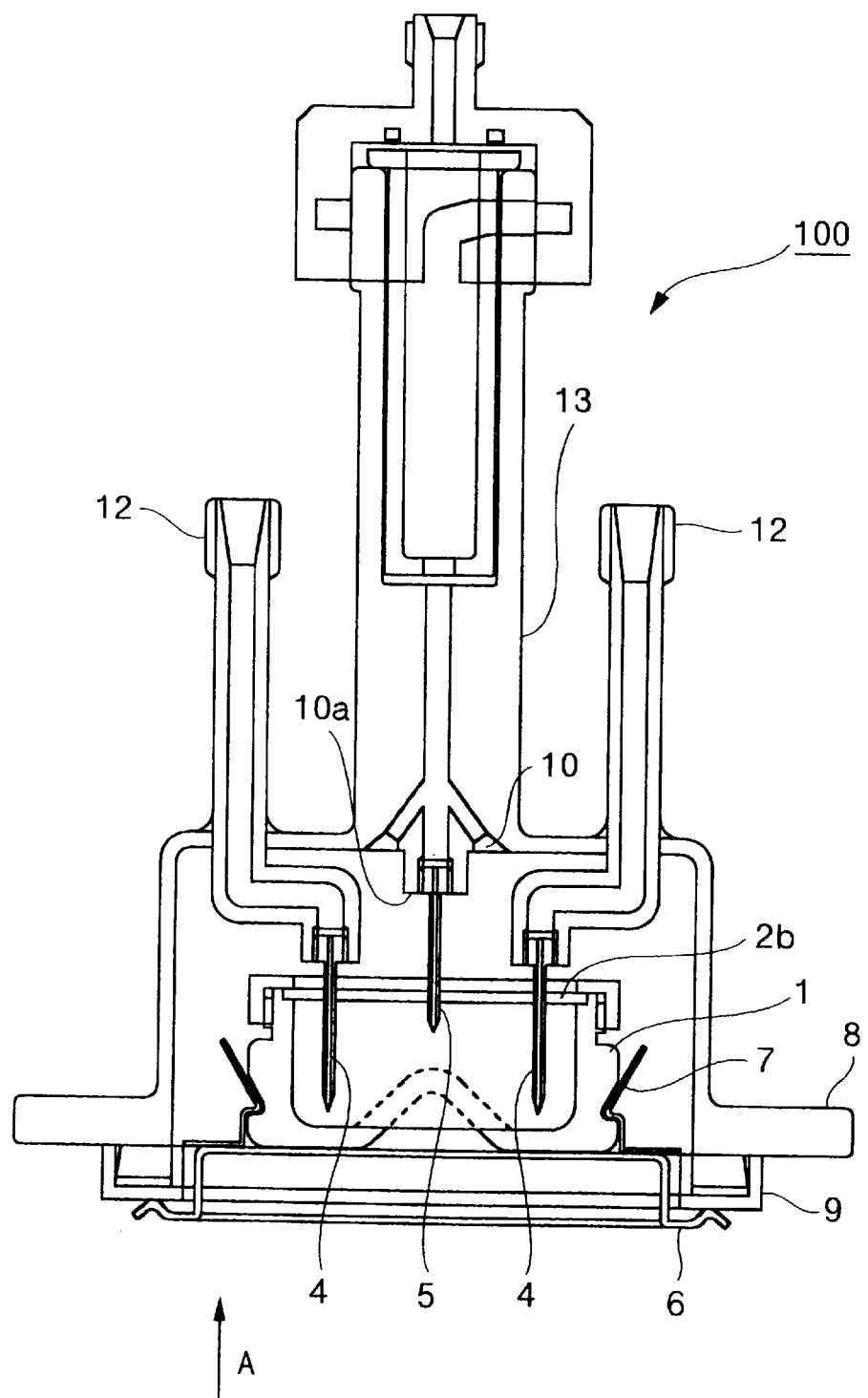
FIG. 5 is a sectional view showing the outline of a heating unit as a fourth aspect of embodiment of the present invention.

The heating unit 100 as shown in FIG. 5 is designed so that it can discharge the vaporized constituents more rapidly than the heating unit 100 of FIG. 4, and has the same configuration as the heating unit 100 as FIG. 2, except that the rubber gasket for the container 1 is a rubber gasket 2b having some degree of permeability. With this configuration, the vaporized constituents and the carrier gas are rapidly discharged from the discharge tube 13 through the rubber gasket 2b and the needle 5 having a through-hole. With the heating unit 100 as shown in FIG. 5, the seal 9 must, of course, be able to hermetically seal the chamber 8a. In FIG. 5, the same reference Nos. as those in FIGS. 2 to 4 denote the same or equivalent portions.

It is desirable that the catch 7 be made of a material having a significant elasticity, because the catch 7 must serve as a catch strong enough to overcome the friction of the needles 4 and 5 in lowering the container 1 together with the sample tray 6 after the discharge of the vaporized constituents is completed.

As the carrier gas, nitrogen or other gas can be used.

As a material for the rubber gasket 2b having some degree of permeability, such a material as "Gore-Tex" rubber manufactured by Nippon Pillar Packing Co., Ltd can be used.

With the heating unit of the present invention, the constituents vaporized from a sample such as an easy-to-vaporize, liquid can be exactly discharged. The heating unit of the present invention has a simple configuration, allowing the vaporized constituents to be discharged rapidly. Particularly, the constituents vaporized from an easy-to-vaporize liquid sample can be discharged without being affected by the atmosphere. Thus, when the heating unit is used for moisture content determination, a substantial improvement in measurement accuracy can be achieved, and when the moisture content is extremely low, it can be determined with high accuracy.

What is claimed:

1. A heating unit, comprising:

a heating tube having a heater for heating a chamber inside said heating tube;

a container for containing a vaporizable sample, said container having an opening that is sealed with a permeable rubber gasket, and said container being disposed in said chamber of said heating tube;

a seal hermetically sealing said chamber with said container therein;

introduction tubes for introducing a carrier gas from outside of said chamber into said container in said chamber, wherein said introduction tubes comprise a needle having a throughhole at an end thereof for piercing said rubber gasket of said container for introduction of the carrier gas into said container; and a discharge tube for discharging vaporized constituents and the carrier gas from said container in said chamber to outside of said chamber, wherein said discharge tube comprises a needle having a through-hole at an end thereof for piercing said rubber gasket of said container and for discharging the vaporized constituents and the carrier gas.

2. A heating unit, comprising:

a heating tube having a heater for heating a chamber inside said heating tube;

a container for containing a vaporizable sample, said container having an opening that is sealed with a permeable rubber gasket, and said container being disposed in said chamber of said heating tube;

a seal hermetically sealing said chamber with said container therein;

introduction tubes for introducing a carrier gas from outside of said chamber into said container in said chamber, wherein said introduction tubes comprise a needle having a throughhole at an end thereof for piercing said rubber gasket of said container for introduction of the carrier gas into said container; and a discharge tube for discharging vaporized constituents and the carrier gas from said container in said chamber to outside of said chamber.

* * * * *